United States Patent
Iwanaga et al.

(10) Patent No.: US 10,194,790 B2
(45) Date of Patent: Feb. 5, 2019

(54) ENDOSCOPE REPROCESSOR, ENDOSCOPE CLEANING TUBE, AND ENDOSCOPE REPROCESSING UNIT

(71) Applicant: OLYMPUS CORPORATION, Tokyo (JP)

(72) Inventors: Naoki Iwanaga, Saitama (JP); Tomohiko Nakao, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/592,303

(22) Filed: May 11, 2017

(65) Prior Publication Data

US 2017/0238794 A1 Aug. 24, 2017

Related U.S. Application Data

(63) Continuation of application No. PCT/JP2016/077702, filed on Sep. 20, 2016.

(30) Foreign Application Priority Data

Dec. 1, 2015 (JP) ................................. 2015-235053

(51) Int. Cl.
*B08B 3/04* (2006.01)
*A61B 1/12* (2006.01)
(Continued)

(52) U.S. Cl.
CPC ............. *A61B 1/121* (2013.01); *A61B 1/12* (2013.01); *A61B 1/123* (2013.01); *B08B 3/12* (2013.01);
(Continued)

(58) Field of Classification Search
CPC ....... A61B 1/123; A61B 1/125; A61L 2202/24; B08B 9/023; B08B 9/0321; B08B 9/0323; B08B 9/0325
See application file for complete search history.

(56) References Cited

U.S. PATENT DOCUMENTS

| | | | | |
|---|---|---|---|---|
| 2005/0209507 A1* | 9/2005 | Suzuki | ................ | A61B 1/123 600/133 |
| 2007/0107152 A1* | 5/2007 | Noguchi | ................ | A61B 1/122 15/104.095 |

(Continued)

FOREIGN PATENT DOCUMENTS

| | | |
|---|---|---|
| CN | 1964665 A | 5/2007 |
| CN | 101011235 A | 8/2007 |

(Continued)

OTHER PUBLICATIONS

JP2006006568—Machine Translation (Year: 2006).*

*Primary Examiner* — Marc Lorenzi
(74) *Attorney, Agent, or Firm* — Scully, Scott, Murphy & Presser, P.C.

(57) ABSTRACT

An endoscope reprocessor includes: a connector to which an endoscope is connected; a fluid supplying section that supplies fluid to the connector; an electromagnet arranged at the connector and including a magnetic material and a coil wound around the magnetic material; a current supplying section; a magnetic force switching portion configured to switch a strength of a magnetic force to at least one of a first strength and a second strength weaker than the first strength; and a control section configured to switch the strength of the magnetic force by controlling the magnetic force switching portion while driving the fluid supplying section.

3 Claims, 8 Drawing Sheets

(51) Int. Cl.
*B08B 3/12* (2006.01)
*B08B 9/023* (2006.01)
*B08B 9/032* (2006.01)

(52) U.S. Cl.
CPC ............ *B08B 9/023* (2013.01); *B08B 9/0323* (2013.01); *B08B 9/0325* (2013.01)

(56) References Cited

U.S. PATENT DOCUMENTS

| | | | | |
|---|---|---|---|---|
| 2007/0185385 A1* | 8/2007 | Noguchi | ................ | A61B 1/123 600/132 |
| 2007/0193605 A1 | 8/2007 | Kuroshima et al. | | |
| 2009/0090398 A1 | 4/2009 | Onishi | | |
| 2009/0217956 A1* | 9/2009 | Noguchi | ................ | A61B 1/123 134/57 R |

FOREIGN PATENT DOCUMENTS

| | | | | |
|---|---|---|---|---|
| JP | 2006006568 A | * | 1/2006 | ............ A61B 1/125 |
| JP | 2008-161383 A | | 7/2008 | |
| JP | 2013-111446 A | | 6/2013 | |

\* cited by examiner

ENDOSCOPE REPROCESSOR, ENDOSCOPE CLEANING TUBE, AND ENDOSCOPE REPROCESSING UNIT

CROSS REFERENCE TO RELATED APPLICATION

This application is a continuation application of PCT/JP2016/077702 filed on Sep. 20, 2016 and claims benefit of Japanese Application No. 2015-235053 filed in Japan on Dec. 1, 2015, the entire contents of which are incorporated herein by this reference.

BACKGROUND OF THE INVENTION

1. Field of the Invention

The present invention relates to an endoscope reprocessor, an endoscope cleaning tube, and an endoscope reprocessing unit.

2. Description of the Related Art

As disclose in Japanese Patent Application Laid-Open Publication No. 2013-111446, an endoscope cleaning apparatus has been conventionally used, in which an endoscope cleaning tube is attached to a pipe sleeve of an endoscope through a cleaning adapter and disinfectant solution is sent from the endoscope cleaning tube to clean the contaminated endoscope.

The cleaning adapter includes a guide pipe having at the distal end thereof a main stream exit and a branched stream exit of disinfectant solution, and the cleaning adapter is attached to the endoscope by the distal end of the guide pipe being inserted into the pipe sleeve of the endoscope. When the disinfectant solution is sent into the cleaning adapter, the guide pipe moves up and down in the pipe sleeve by the change of pressure of the sent disinfectant solution such that the inner circumference and the outer circumference of the pipe sleeve can be exposed to the disinfectant solution, and the guide pipe causes the disinfectant solution to be discharged from the main stream exit and the branched stream exit.

SUMMARY OF THE INVENTION

An endoscope reprocessor according to one aspect of the present invention includes: a connector to which an endoscope is connected directly or through a tube; a fluid supplying section that supplies fluid to the connector; an electromagnet arranged at the connector and including a magnetic material and a coil wound around the magnetic material; a current supplying section that applies current to the coil; a magnetic force switching portion connected to the electromagnet, and configured to switch a strength of a magnetic force to at least one of a first strength and a second strength weaker than the first strength; and a control section connected to the magnetic force switching portion and the fluid supplying section, and configured to switch the strength of the magnetic force by controlling the magnetic force switching portion while driving the fluid supplying section.

An endoscope cleaning tube according to one aspect of the present invention includes: an endoscope-side connection portion connected to an endoscope; a connector-side connection portion connected to a connector of an endoscope reprocessor including a connector to which an endoscope is connected directly or through a tube, a fluid supplying section that supplies fluid to the connector, an electromagnet arranged at the connector and including a magnetic material and a coil wound around the magnetic material, a current supplying section that applies current to the coil, a magnetic force switching portion connected to the electromagnet, and configured to switch a strength of a magnetic force to at least one of a first strength and a second strength weaker than the first strength, and a control section connected to the magnetic force switching portion and the fluid supplying section, and configured to switch the strength of the magnetic force by controlling the magnetic force switching portion while driving the fluid supplying section; a tube body connecting the endoscope-side connection portion and the connector-side connection portion; and an electromagnet attraction portion made of metal and arranged at the connector-side connection portion.

An endoscope reprocessing unit according to one aspect of the present invention is an endoscope reprocessing unit including an endoscope reprocessor and an endoscope cleaning tube, wherein a connector-side connection portion includes an insertion port into which a connector is inserted, and a connector includes, on an outer wall thereof, a flow passage and a watertight portion, the flow passage being separated from an inner wall of the connector-side connection portion and discharging, from an insertion port, fluid supplied from a fluid supplying section when a strength of a magnetic force is a second strength, the watertight portion being brought into close contact with the inner wall of the connector-side connection portion and closing the flow passage when the strength of the magnetic force is a first strength.

DETAILED DESCRIPTION OF THE PREFERRED EMBODIMENTS

Hereinafter, embodiments of the present invention will be described with reference to drawings.

First Embodiment (Configuration)

Figure 1:
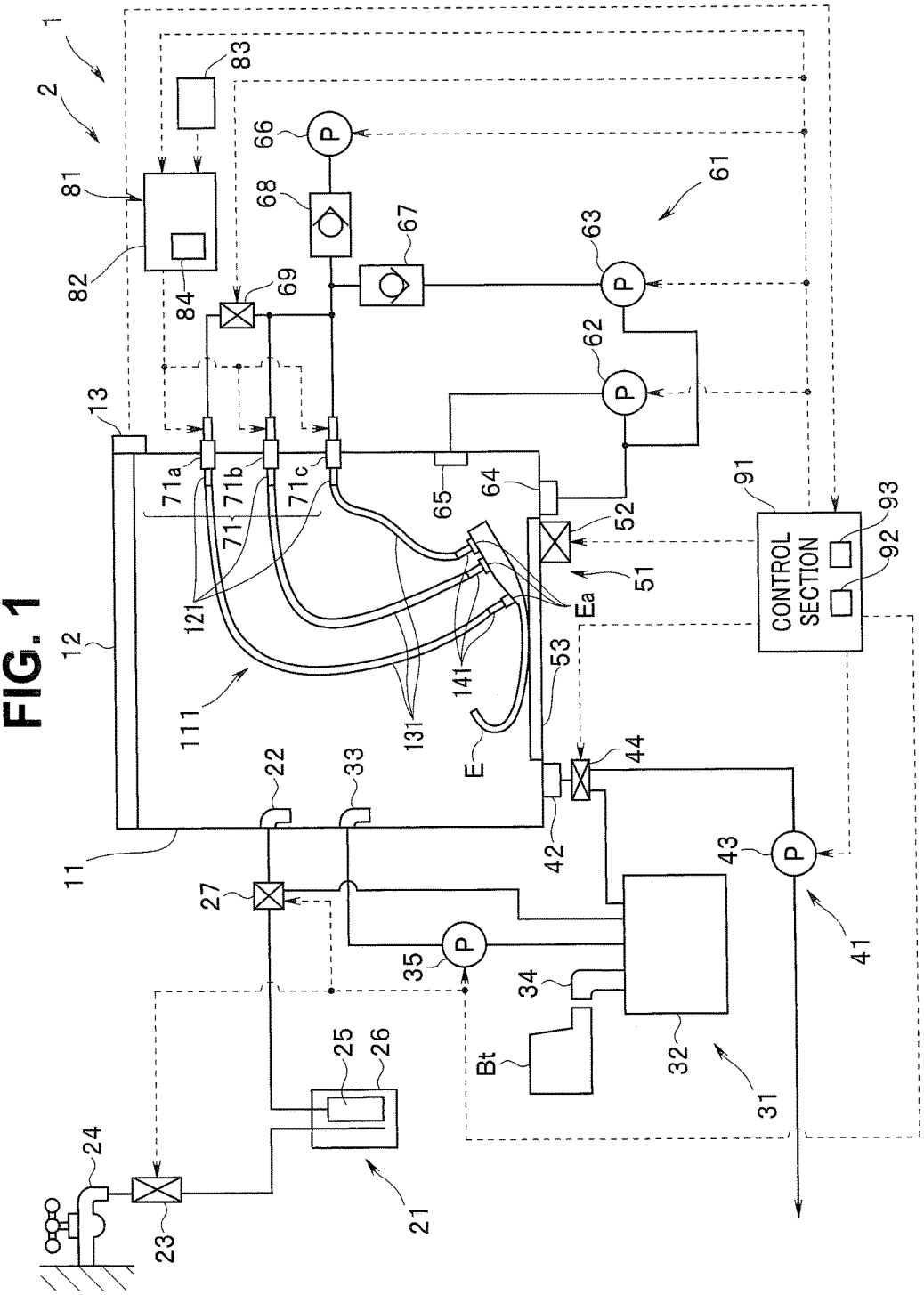
FIG. 1 is a block diagram illustrating a schematic configuration of a main part of an endoscope reprocessing unit according to a first embodiment of the present invention.

FIG. 1 is a block diagram illustrating a schematic configuration of a main part of an endoscope reprocessing unit 1 according to the first embodiment of the present invention. In FIG. 1, conduits are shown with solid lines, and electric signal lines are shown with dashed lines.

As shown in FIG. 1, the endoscope reprocessing unit 1 includes an endoscope reprocessor 2, and an endoscope cleaning tube 111 which is a tube. The endoscope reprocessor 2 is connected with an endoscope E through the endoscope cleaning tube 111.

The main part of the endoscope reprocessor 2 is configured by a processing tank 11, a water supplying section 21, a medicinal solution supplying section 31, a liquid drainage section 41, an ultrasound vibration section 51, a fluid supplying section 61, connectors 71a, 71b, and 71c as a connection section (hereinafter, referred to as connector 71 when indicating any one of the connectors, or indicating all of the three connectors), a current supplying section 81, and a control section 91.

The endoscope reprocessor 2 is an apparatus that performs reprocess processing on the contaminated endoscope E or endoscope accessories, not shown. The reprocess processing referred to here is not specifically limited, and may be any of rinsing with water, cleaning for removing dirt such as organic substances, disinfection for disabling predetermined microorganisms, sterilization for eliminating or killing all the microorganisms, or a combination of any of these.

The processing tank 11 is formed in a tub shape so that one or a plurality of endoscopes E can be placed inside the tub and liquid can be stored. The processing tank 11 includes a lid portion 12 and an open/close detection portion 13.

The lid portion 12 is configured to be openable and closable with respect to the processing tank 11.

The open/close detection portion 13 is configured to be capable of detecting opening and closing of the lid portion 12 by using a sensor, a switch, or the like, for example. The open/close detection portion 13 is connected to the control section 91. The open/close detection portion 13 detects the open state and the closed state of the lid portion 12, and outputs a control signal indicating the open state or the closed state of the lid portion 12 to the control section 91.

The water supplying section 21 is connected to the processing tank 11 through a water supplying port 22, and configured to be capable of supplying water to the processing tank 11. The water supplying section 21 takes in water from an external water supply source 24 through a water supply valve 23 that is opened and closed under control by the control section 91, filters the water through a filter 26 in which a filter cartridge 25 is contained, and supplies the water from the water supplying port 22 to the processing tank 11. When the conduit is switched by a conduit switching valve 27 for which switching control is performed by the control section 91, the water filtered through the filter 26 is supplied to a tank 32.

The medicinal solution supplying section 31 is connected to the processing tank 11 through a medicinal solution supplying port 33, and configured to be capable of supplying medicinal solution to the processing tank 11. The medicinal solution supplying section 31 includes a bottle attaching portion 34 to which a bottle Bt is attached, and is capable of taking in concentrated disinfectant solution from the attached bottle Bt to the tank 32. The concentrated disinfectant solution taken into the tank 32 is diluted by the water supplied through the conduit switching valve 27, to be disinfectant solution and stored in the tank 32. The disinfectant solution stored in the tank 32 is supplied from the medicinal solution supplying port 33 to the processing tank 11 with a medicinal solution pump 35 driven and controlled by the control section 91.

The liquid drainage section 41 is connected to the processing tank 11 through a liquid drainage port 42, and configured to be capable of discharging the liquid stored in the processing tank 11 from the processing tank 11. The liquid drainage section 41 includes a liquid drainage pump 43 that is driven and controlled by the control section 91, and the liquid drainage pump 43 is driven to cause the liquid in the processing tank 11 to be discharged from the liquid drainage port 42 to external liquid drainage means. When the conduit is switched by a conduit switching valve 44 for which switching control is performed by the control section 91, the liquid stored in the processing tank 11 flows into the tank 32 and stored in the tank 32 in preparation for reuse.

The ultrasound vibration section 51 is configured to be capable of outputting ultrasound to the liquid stored in the processing tank 11. The ultrasound vibration section 51 includes an ultrasound transducer 52, and a vibration plate 53 connected to the ultrasound transducer 52. When the ultrasound transducer 52 vibrates the vibration plate 53 under the drive control by the control section 91, the vibration plate 53 outputs ultrasound to the liquid stored in the processing tank 11.

The fluid supplying section 61 is configured to be capable of supplying fluid to the connector 71. The fluid supplying section 61 sucks the liquid stored in the processing tank 11 from a circulation suction port 64 and discharges the sucked liquid from a liquid discharge port 65 by using the circulation pump 62 driven and controlled by the control section 91, thereby causing the liquid stored in the processing tank 11 to circulate.

The fluid supplying section 61 is capable of sucking the liquid stored in the processing tank 11 from the circulation suction port 64 and sending the liquid to the connector 71, by using a liquid feeding pump 63 driven and controlled by the control section 91.

The fluid supplying section 61 is capable of taking in gas from outside to send the gas into the connector 71 by an air compressor 66 driven and controlled by the control section 91.

The fluid supplying section 61 includes a check valve 67 for preventing the gas sent from the air compressor 66 from flowing into the liquid feeding pump 63. The fluid supplying section 61 includes a check valve 68 for preventing the liquid sent from the liquid feeding pump 63 from flowing into the air compressor 66.

The fluid supplying section 61 includes an opening/closing valve 69 controlled to be opened and closed by the control section 91 so as to be capable of draining off the water in the conduit of the endoscope E by closing the connector 71a and sending gas from the connectors 71b and 71c under high pressure.

Figure 2:
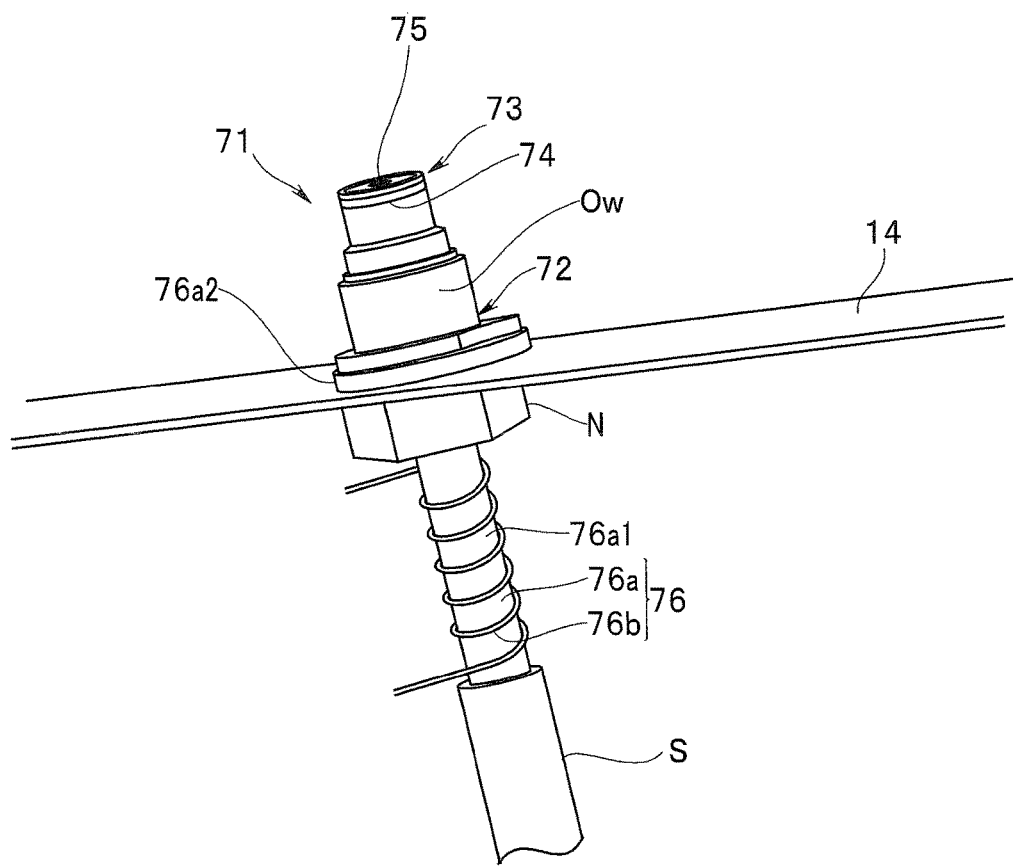
FIG. 2 is a perspective view showing an appearance configuration of a connector of the endoscope reprocessor according to the first embodiment of the present invention.
Figure 3:
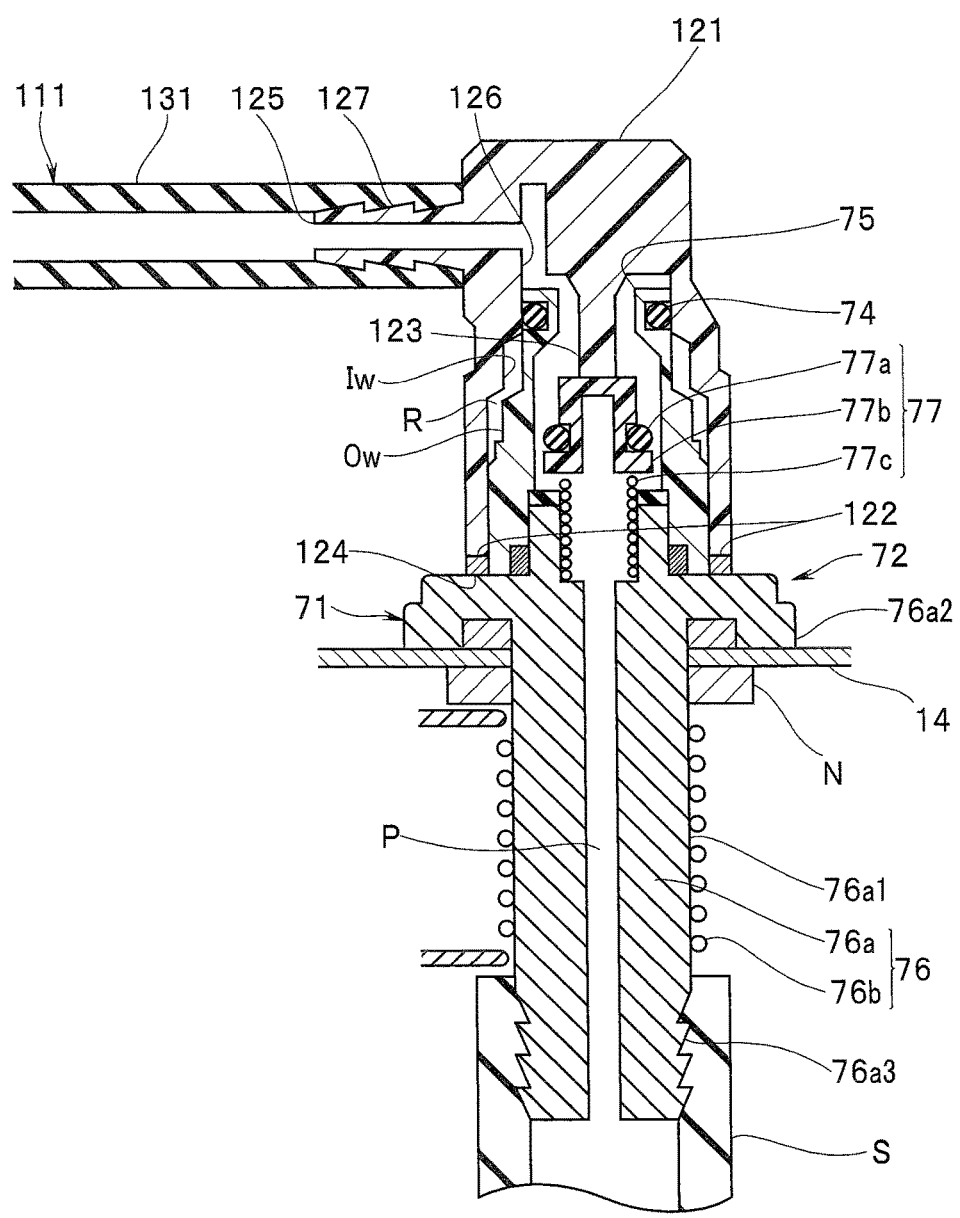
FIG. 3 is a cut end face view showing a configuration of the connector of the endoscope reprocessor and a connector-side connection portion of an endoscope cleaning tube according to the first embodiment of the present invention.
Figure 4:
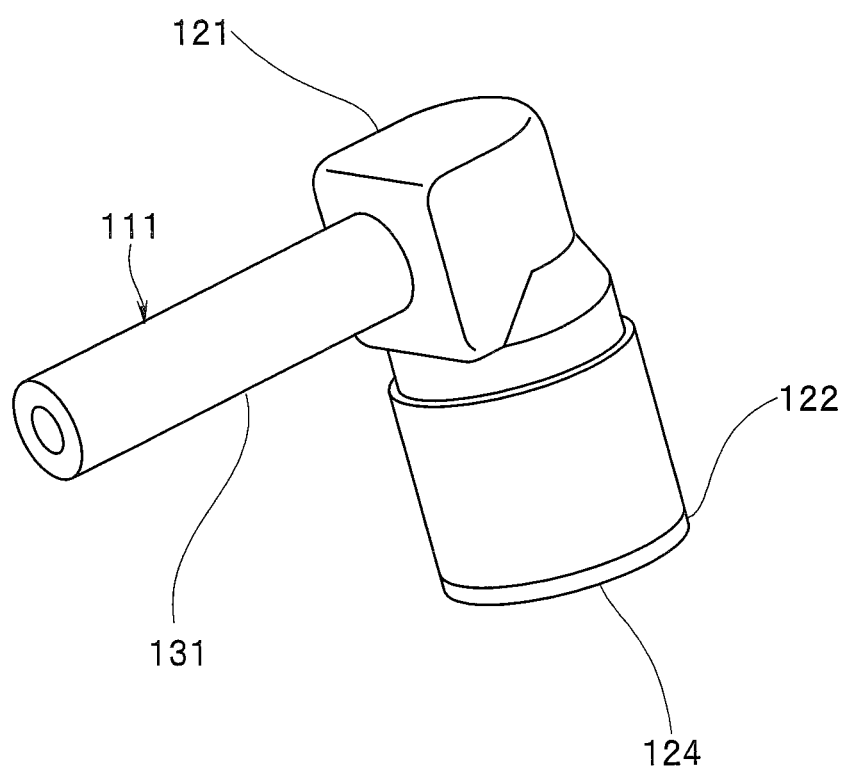
FIG. 4 is a perspective view showing an appearance configuration of the connector-side connection portion of the endoscope cleaning tube according to the first embodiment of the present invention.

FIG. 2 is a perspective view showing the appearance configuration of the connector 71 of the endoscope reprocessor 2 according to the first embodiment of the present invention. FIG. 3 is a cut end face view showing the configuration of the connector 71 of the endoscope reprocessor 2 and a connector-side connection portion 121 of the endoscope cleaning tube 111 according to the first embodiment of the present invention. FIG. 4 is a perspective view showing the appearance configuration of the connector-side connection portion 121 of the endoscope cleaning tube 111 according to the first embodiment of the present invention. FIG. 4 shows the state where the endoscope cleaning tube 111 is attached to the connector-side connection portion 121.

The connector 71 is arranged on the processing tank 11 and configured so that the endoscope E can be connected thereto directly or through the endoscope cleaning tube 111. The endoscope reprocessor 2 is capable of supplying fluid, through the connector 71, to the connected endoscope E.

As shown in FIG. 2, the connector 71 is provided on a wall board 14 of the processing tank in a protruded manner. The connector 71 includes a base portion 72 formed to be thick and a distal portion 73 formed to be thin, and has a level difference on an outer wall Ow. The connector 71 includes an O-ring 74 as a watertight portion on the outer wall Ow of the distal portion 73. The connector 71 includes on the distal end surface thereof a discharge port 75.

As shown in FIG. 3, the connector 71 includes an electromagnet 76 and a valve 77.

The electromagnet 76 is arranged at the base portion 72 of the connector 71, and includes a core 76a made of a magnetic material and a coil 76b wound around the core 76a.

The core 76a is made of a magnetic material such as iron, for example. The core 76a is fixed to the wall board 14 of the processing tank with a nut N. The core 76a includes a cylindrical body 76a1 and a receiving portion 76a2.

The cylindrical body 76a1 includes at the proximal end thereof an anti-slipping protrusion 76a3 so that a hose S can be connected. The cylindrical body 76a1 includes inside thereof a fluid conduit P through which the fluid supplied from the hose S flows. The cylindrical body 76a1 includes the coil 76b wound around the outer circumference thereof, and is configured to be capable of generating an electromagnetic attraction force that is a magnetic force.

The receiving portion 76a2 is formed by expanding the distal end of the cylindrical body 76a1 in a flanged shape. The receiving portion 76a2 is configured to be capable of attracting an electromagnet attraction portion 122 of the connector-side connection portion 121 of the endoscope cleaning tube 111 with an electromagnetic attraction force, to thereby receive the electromagnet attraction portion 122.

The coil 76b is made of a material such as copper. The coil 76b is wound around the outer circumference of the cylindrical body 76a1 by a predetermined number of turns A. The predetermined number of turns A is set in advance to a number of turns such that the coil can generate an electromagnetic attraction force for attracting the electromagnet attraction portion 122.

The valve 77 includes a valve body 77b having an O-ring 77a on the outer circumference thereof, and a compression spring 77c that biases the valve body 77b.

With reference back to FIG. 1, the current supplying section 81 is a circuit that applies current to the coil 76b. The current supplying section 81 includes a magnetic force switching portion 82 and a power source 83.

The magnetic force switching portion 82 includes a drive circuit 84 as a voltage switching portion so as to be capable of adjusting the amount of the current to be supplied to the electromagnet 76 by switching the output voltage. The magnetic force switching portion 82 is connected to the power source 83 and the control section 91. The magnetic force switching portion 82 receives power from the power source 83, and adjusts the amount of the current, to apply the current to the coil 76b under the control by the control section 91. The magnetic force switching portion 82 is connected to the electromagnet 76, and is capable of switching the strength of magnetic force generated by the electromagnet 76 to a strength among a plurality of strengths.

For example, the magnetic force switching portion 82 is capable of switching the strength of the magnetic force generated by the electromagnet 76 at least one of a first strength and a second strength weaker than the first strength. Furthermore, the magnetic force switching portion 82 is capable of switching the strength of the magnetic force generated by the electromagnet 76 to a third strength weaker than the second strength. More specifically, the drive circuit 84 switches the output voltage to any one of a predetermined voltage VH, a predetermined voltage VM lower than the predetermined voltage VH, and a predetermined voltage VL lower than the predetermined voltage VM, and thereby the electromagnetic attraction force of the electromagnet 76 is switched to one of the first strength, the second strength, and the third strength in accordance with the switched output voltage.

The first strength is set to the strength of the electromagnetic attraction force at which the electromagnet 76 attracts the electromagnet attraction portion 122 when the fluid is sent to the endoscope E.

The second strength is set to the strength of the electromagnetic attraction force at which the electromagnet attraction portion 122 is separated from the electromagnet 76 when the fluid is sent to the endoscope E.

The third strength is smaller than the second strength, and set to the strength of the electromagnetic attraction force at which the connector-side connection portion 121 is temporarily fixed in the state where the connector-side connection portion 121 can be easily detached with fingers, when the fluid is not supplied to the endoscope E.

The control section 91 includes a central processing unit (hereinafter, referred to as "CPU") 92, and a memory 93 such as ROM, RAM, or the like. The function of the CPU 92 is implemented by executing a program related to the processing of cleaning and disinfecting of the endoscope E, which is stored in the memory 93. The control section 91 is connected to the water supply valve 23, the conduit switching valves 27, 44, the medicinal solution pump 35, the water drainage pump 43, the ultrasound transducer 52, the circulation pump 62, the liquid feeding pump 63, the air compressor 66, the opening/closing valve 69, the magnetic force switching portion 82, and the open/close detection portion 13.

The control section 91 is capable of controlling the magnetic force switching portion 82 to switch the strength of the magnetic force while driving the fluid supplying section 61 including the circulation pump 62 and the liquid feeding pump 63. More specifically, the control section 91 controls the magnetic force switching portion 82 to cause the magnetic force switching portion 82 to switch the strength of the magnetic force generated by the electromagnet 76 alternately between the first strength and the second strength, for example, while driving and controlling the fluid supplying section 61 to cause the fluid supplying section 61 to supply fluid to the processing tank 11. Furthermore, the control section 91 is capable of controlling the magnetic force switching portion 82 to cause the magnetic force switching portion 82 to set the strength of the magnetic force to the third strength during the detection of the opening of the lid portion 12 by the open/close detection portion 13.

The endoscope cleaning tube 111 includes the connector-side connection portion 121, a tube body 131, and an endoscope-side connection portion 141.

The endoscope-side connection portion 141 is configured so as to be connectable to a pipe sleeve Ea of the endoscope E.

The tube body 131 is made of a material such as rubber, synthetic resin, or the like and formed in an elongated cylindrical shape. The tube body 131 has one end portion to which the connector-side connection portion 121 is connected and the other end portion to which the endoscope-side connection portion 141 is connected.

The connector-side connection portion 121 is connectable to the connector 71 of the endoscope reprocessor 2, as shown in FIGS. 3 and 4. The connector-side connection portion 121 includes an insertion port 124 and a tube connection port 125.

The insertion port 124 is formed in a cylindrical shape so as to be able to be fitted to the outside of the connector 71 of the endoscope reprocessor 2. The insertion port 124 includes the electromagnet attraction portion 122, a narrowing portion 126, and a pushing rod 123.

The electromagnet attraction portion 122 is made of a metal magnetic material such as iron, for example. The electromagnet attraction portion 122 is formed in a ring shape, and arranged at the opening end of the insertion port 124. The electromagnet attraction portion 122 is attracted by the electromagnetic attraction force of the electromagnet 76.

The narrowing portion 126 is formed such that the inner wall Iw of the insertion port 124 becomes narrower at the deep part of the insertion port 124 than the inner wall of the other part of the insertion port 124.

The pushing rod 123 is formed in a rod shape so as to be protruded from the deep part of the insertion port 124 in the direction of the opening end of the insertion port 124.

When the connector-side connection portion 121 is attached to the connector 71, the pushing rod 123 pushes the valve body 77b against the biasing force of a compression spring 77c, and the valve 77 is brought into a valve-open state. On the other hand, when the connector-side connection portion 121 is detached from the connector 71, the O-ring 77a of the valve body 77b is abutted against the narrowing portion 126 by the compression spring 77c, and the valve 77 is brought into a valve-closed state.

The tube connection port 125 includes on the outer circumference thereof an anti-slipping protrusion 127 such that the tube body 131 can be connected.

When the connector-side connection portion 121 is attached to the connector 71, a flow passage R is formed between the outer wall Ow of the connector 71 and the inner wall Iw of the connector-side connection portion 121.

(Working)

Next, the working of the endoscope reprocessing unit 1 will be described.

Figure 5:
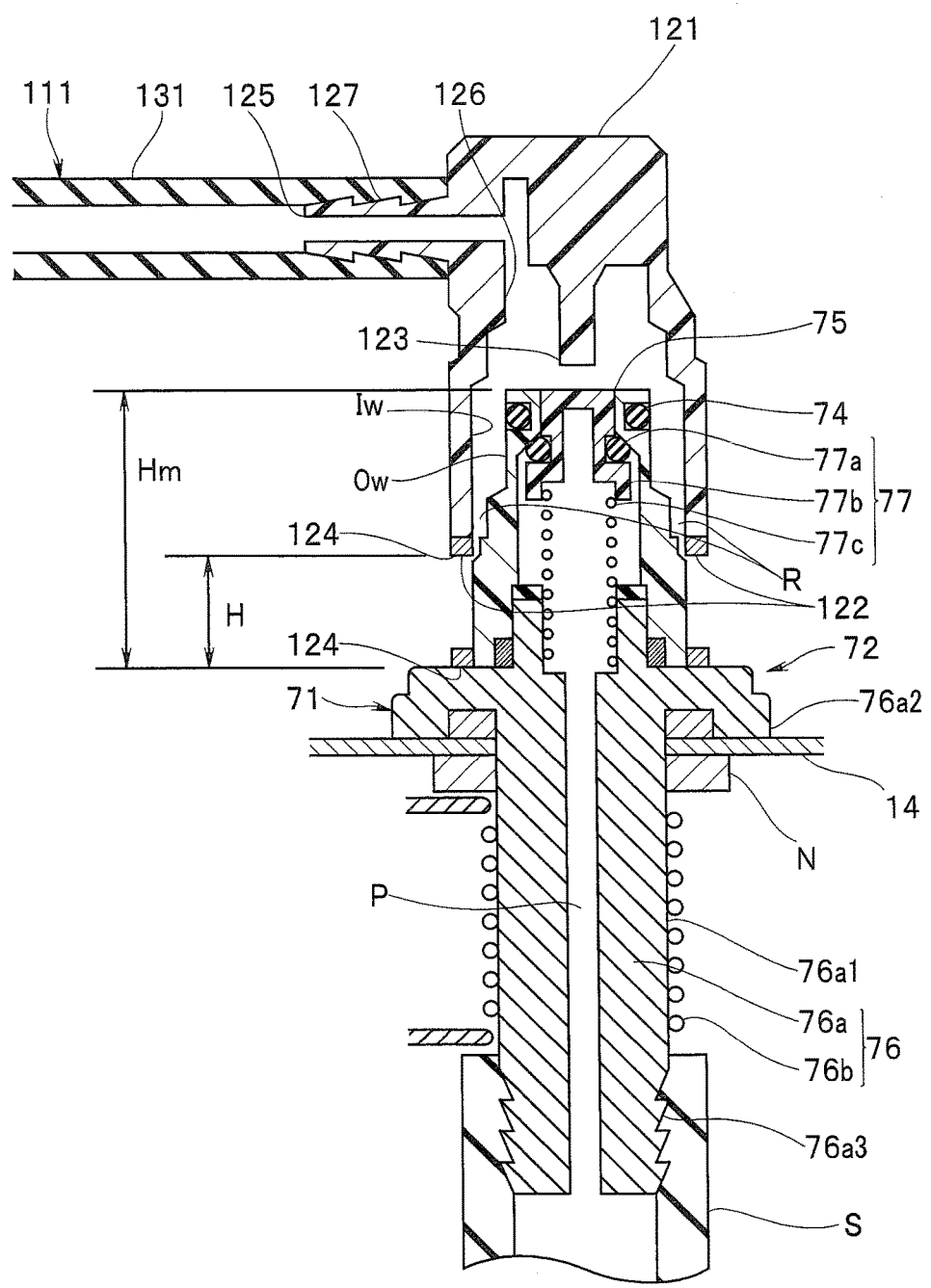
FIG. 5 is a cut end face view showing a configuration of the connector of the endoscope reprocessor and the connector-side connection portion of the endoscope cleaning tube according to the first embodiment of the present invention.
Figure 6:
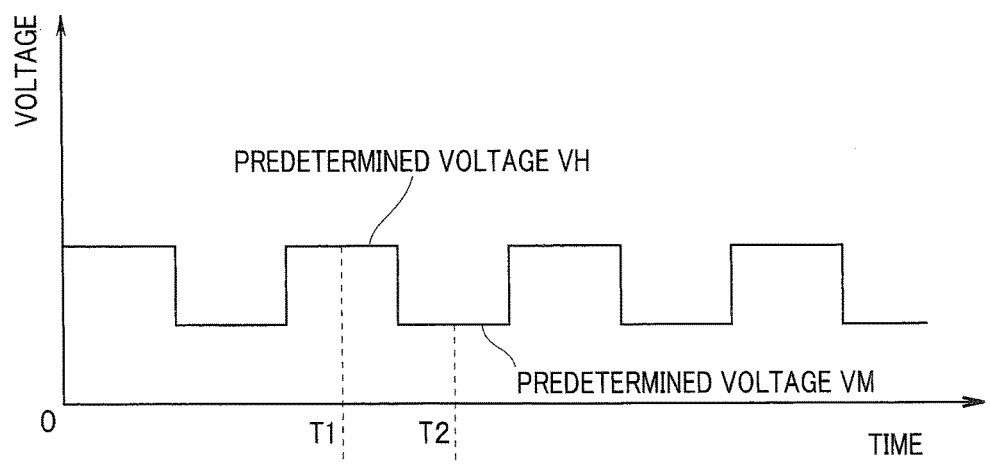
FIG. 6 is a graph showing a relation between liquid feeding time of the endoscope reprocessor and a height of the electromagnet attraction portion, according to the first embodiment of the present invention.
Figure 6:
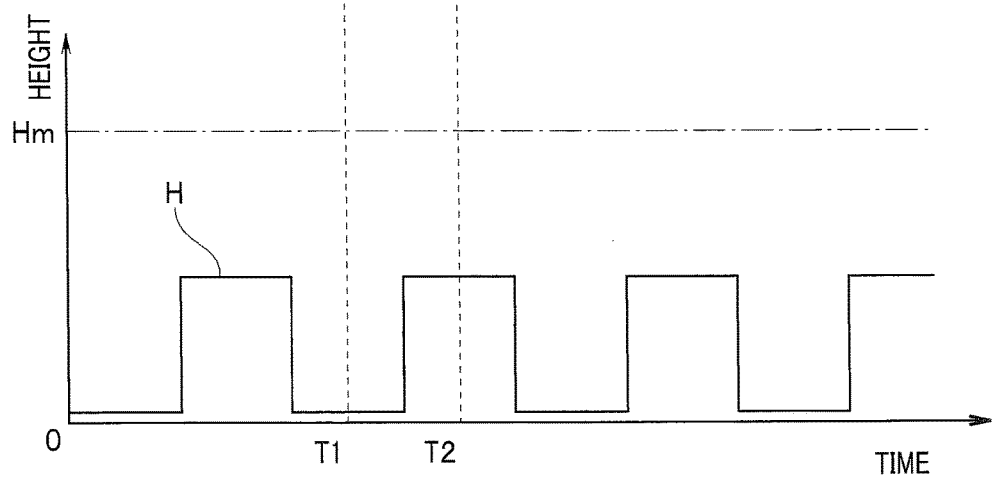

FIG. 5 is a cut end face view showing the configuration of the connector 71 of the endoscope reprocessor 2 and the connector-side connection portion 121 of the endoscope cleaning tube 111 according to the first embodiment of the present invention. FIG. 6 is a graph showing a relation between the liquid feeding time of the endoscope reprocessor 2 and the height H of the electromagnet attraction portion 122, according to the first embodiment of the present invention. In FIGS. 5 and 6, the height H indicates the height from the receiving portion 76a2 to the electromagnet attraction portion 122, and the height Hm indicates the height from the receiving portion 76a2 to the distal end of the connector 71.

When a user opens the lid portion 12 so that the endoscope E can be set, the open/close detection portion 13 detects the open state of the lid portion 12, and outputs a control signal indicating that the lid portion 12 is in the open state to the control section 91. When the control signal indicating that the lid portion 12 is in the open state is inputted, the control section 91 outputs a control signal for setting the output voltage of the drive circuit 84 to the predetermined voltage VL to the magnetic force switching portion 82, to switch the strength of the electromagnetic attraction force of the electromagnet 76 to the third strength. When the user places the connector-side connection portion 121 on the connector 71, the connector-side connection portion 121 is temporarily fixed to the connector 71 by the electromagnetic attraction force of the electromagnet 76.

The control section 91 outputs a control signal for setting the output voltage of the drive circuit 84 to the predetermined voltage VH to the magnetic force switching portion 82, to switch the strength of the electromagnetic attraction force of the electromagnet 76 of the connector 71 to the first strength. When the strength of the electromagnet attraction force of the electromagnet 76 reaches the first strength, the electromagnet attraction portion 122 of the connector-side connection portion 121 of the endoscope cleaning tube 111 is attracted to the receiving portion 76a2 by the electromagnetic attraction force of the electromagnet 76, and thereby the connector-side connection portion 121 is fitted to the connector 71. Then, the pushing rod 123 of the connector-side connection portion 121 pushes the valve body 77b of the connector 71 against the biasing force of the compression spring 77c, to thereby bring the valve 77 into the valve-open state. When the strength of the electromagnetic attraction force is the first strength, the O-ring 77a of the connector 71 closely contacts the inner wall Iw of the connector-side connection portion 121 to close the flow passage R, to thereby prevent the fluid from leaking to the opening end of the connector-side connection portion 121.

The control section 91 outputs a driving signal to the liquid feeding pump 63 or the air compressor 66, to start supply of the fluid at a constant pressure. When the supply of the fluid is started, the fluid flows from the hose S into the fluid conduit P, flows through the compression spring 77c, and discharged from the tube connection port 125, and then sent into the endoscope E through the endoscope cleaning tube 111.

The control section 91 outputs a control signal for setting the output voltage of the drive circuit 84 to the predetermined voltage VM to the magnetic force switching portion 82, to switch the amount of current flowing through the coil 76b, thereby switching the strength of the electromagnetic attraction force of the electromagnet 76 to the second strength weaker than the first strength. When the strength of the electromagnetic attraction force of the electromagnet 76 reaches the second strength, as shown in FIG. 5, the sum of the pressure of the fluid that pushes the connector-side connection portion 121 and the biasing force of the compression spring 77c that pushes the pushing rod 123 through the valve body 77b becomes larger than the electromagnetic attraction force of the electromagnet 76, which causes the electromagnet attraction portion 122 to separate from the receiving portion 76a2 of the connector 71. Then, the inner wall Iw of the connector-side connection portion 121 is separated from the outer wall Ow of the connector 71, and the fluid supplied from the fluid supplying section 61 is discharged from the insertion port 124 via the flow passage R. As a result, the inner wall Iw of the connector-side connection portion 121 and the outer wall Ow of the connector 71 are exposed to the fluid, to be cleaned and disinfected.

After switching the strength of the electromagnetic attraction force to the second strength, the control section 91 switches the strength of the electromagnetic attraction force of the electromagnet 76 back to the first strength so as to prevent the connector-side connection portion 121 from being detached from the connector 71. When the strength of the electromagnetic attraction force of the electromagnet 76 reaches the first strength, the electromagnetic attraction force of the electromagnet 76 becomes larger than the sum of the pressure of the fluid that pushes the connector-side connection portion 121 and the biasing force of the compression spring 77*c* that pushes the pushing rod 123 through the valve body 77*b*, and the electromagnet attraction portion 122 is attracted to the receiving portion 76*a*2 of the connector 71. Note that FIG. 3 illustrates an example of the state where the electromagnet attraction portion 122 is attracted and abutted against the receiving portion 76*a*2.

As shown in FIG. 6, when the output voltage of the drive circuit 84 is the predetermined voltage VH at the time T1, for example, the height H of the electromagnet attraction portion 122 becomes low. On the other hand, when the output voltage of the drive circuit 84 is the predetermined voltage VM at the time T2, for example, the height H of the electromagnet attraction portion 122 becomes high. The height H is controlled so as not to exceed the height Hm (one-dot chain line in FIG. 6) of the connector 71 to prevent the electromagnet attraction portion 122 from being detached from the connector 71.

The control section 91 controls the magnetic force switching portion 82 to repeat switching between the first strength and the second strength, thereby allowing the connector-side connection portion 121 to move reciprocately without being detached from the connector 71, and causes the fluid to flow through the flow passage R between the outer wall Ow of the connector 71 and the inner wall Iw of the connector-side connection portion 121, thereby enabling the outer wall Ow and the inner wall Iw to be cleaned and disinfected.

When cleaning and disinfecting processing of the endoscope E has been finished and a user opens the lid portion 12 to take out the endoscope E, the control section 91 switches the strength of the electromagnetic attraction force of the electromagnet 76 to the third strength so that the connector-side connection portion 121 can be detached from the connector 71.

According to such a configuration, the endoscope reprocessor 2 enables the connector-side connection portion 121 to be attracted the electromagnet 76 by the electromagnetic attraction force, the strength of which is the third strength, and enables the endoscope cleaning tube 111 to be attached and detached with a light force of the fingers.

In addition, the endoscope cleaning tube 111 can be mounted to the endoscope reprocessor 2 even if a claw for connecting the endoscope reprocessor 2 and the cleaning tube 111 is not provided. However, the present invention does not exclude the combination use of such a claw. The endoscope cleaning tube 111 of the present invention may be provided with a claw.

According to the above-described first embodiment, the outer wall Ow of the connector 71 of the endoscope reprocessor 2 and the inner wall Iw of the connector-side connection portion 121 of the endoscope cleaning tube 111 can be cleaned and disinfected with the fluid at the constant pressure that is sent from the endoscope reprocessor 2 to the endoscope E.

Second Embodiment

In the first embodiment, the electromagnetic attraction force generated by the electromagnet 76 is switched by changing the amount of current to be applied to the coil 76*b*. However, a plurality of coils are provided and the coil to which the current is applied may be switched among the plurality of coils.

Figure 7:
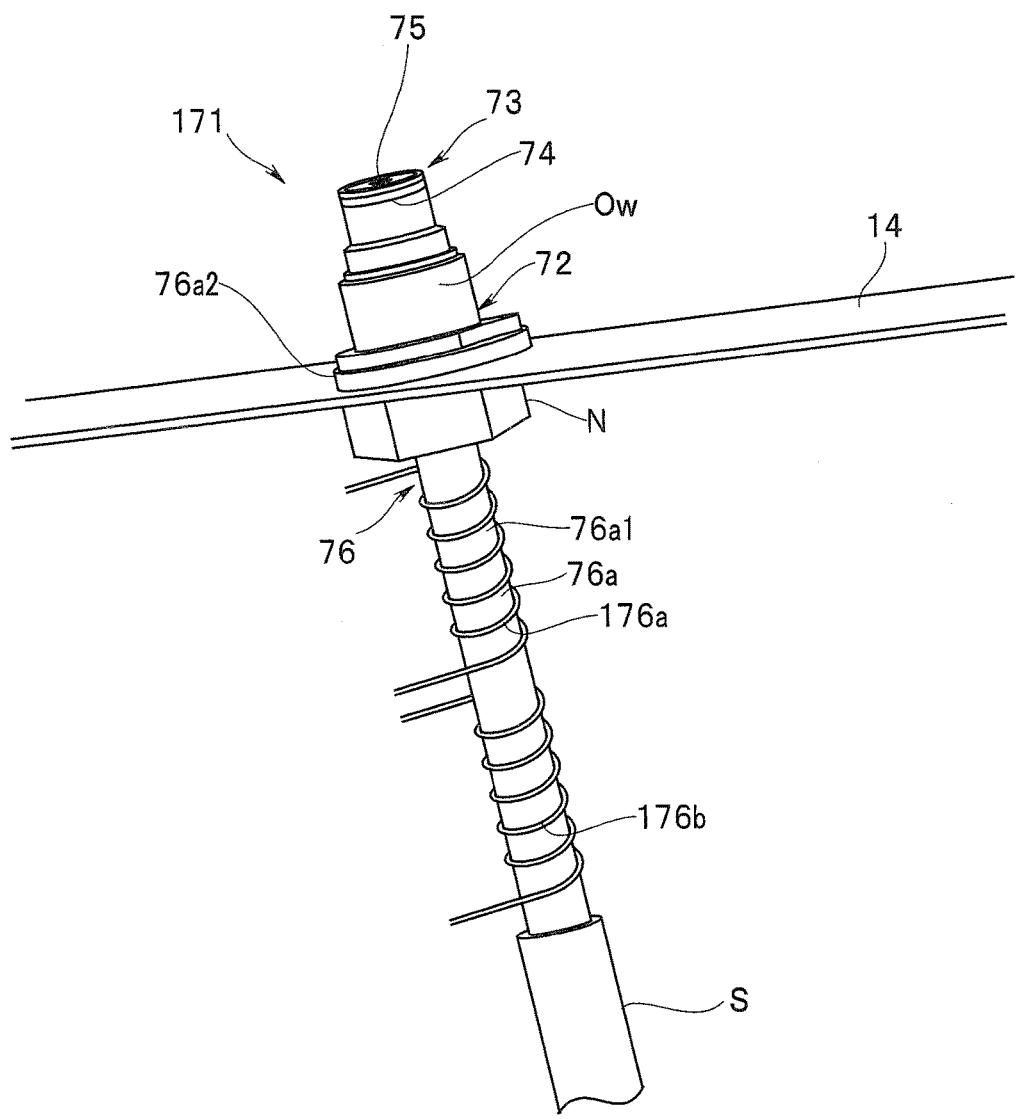
FIG. 7 is a perspective view showing an appearance configuration of a connector of an endoscope reprocessor according to a second embodiment of the present invention.

FIG. 7 is a perspective view showing an appearance configuration of a connector 171 of the endoscope reprocessor 2 according to the second embodiment of the present invention. In the second embodiment, the same components as those in the first embodiment are attached with the same reference numerals and description thereof will be omitted.

The connector 171 includes coils 176*a* and 176*b*. The number of turns of each of the coils 176*a* and 176*b* is set to a predetermined number of turns B. Each of the coils 176*a* and 176*b* is connected to the magnetic force switching portion 82.

The magnetic force switching portion 82 applies current to the coils 176*a* and 176*b* when switching the strength of the electromagnetic attraction force to the first strength, and applies current to the coil 176*b* when switching the strength of the electromagnetic attraction force to the second strength. With such a configuration, the strength of the electromagnetic attraction force of the electromagnet 76 can be switched to one of the first strength and the second strength.

According to the second embodiment, the strength of the electromagnetic attraction force of the electromagnet 76 is switched by switching to which of the coils 176*a* and 176*b* the current is applied, to thereby enable the outer wall Ow of the connector 171 of the endoscope reprocessor 2 and the inner wall Iw of the connector-side connection portion 121 of the endoscope cleaning tube 111 to be cleaned and disinfected with the fluid at the constant pressure that is sent from the endoscope reprocessor 2 to the endoscope E.

Modified Example of Second Embodiment

In the second embodiment, the number of turns of the coil 176*a* is same as that of the coil 176*b*. However, the number of turns of these two coils may be different from each other.

Figure 8:
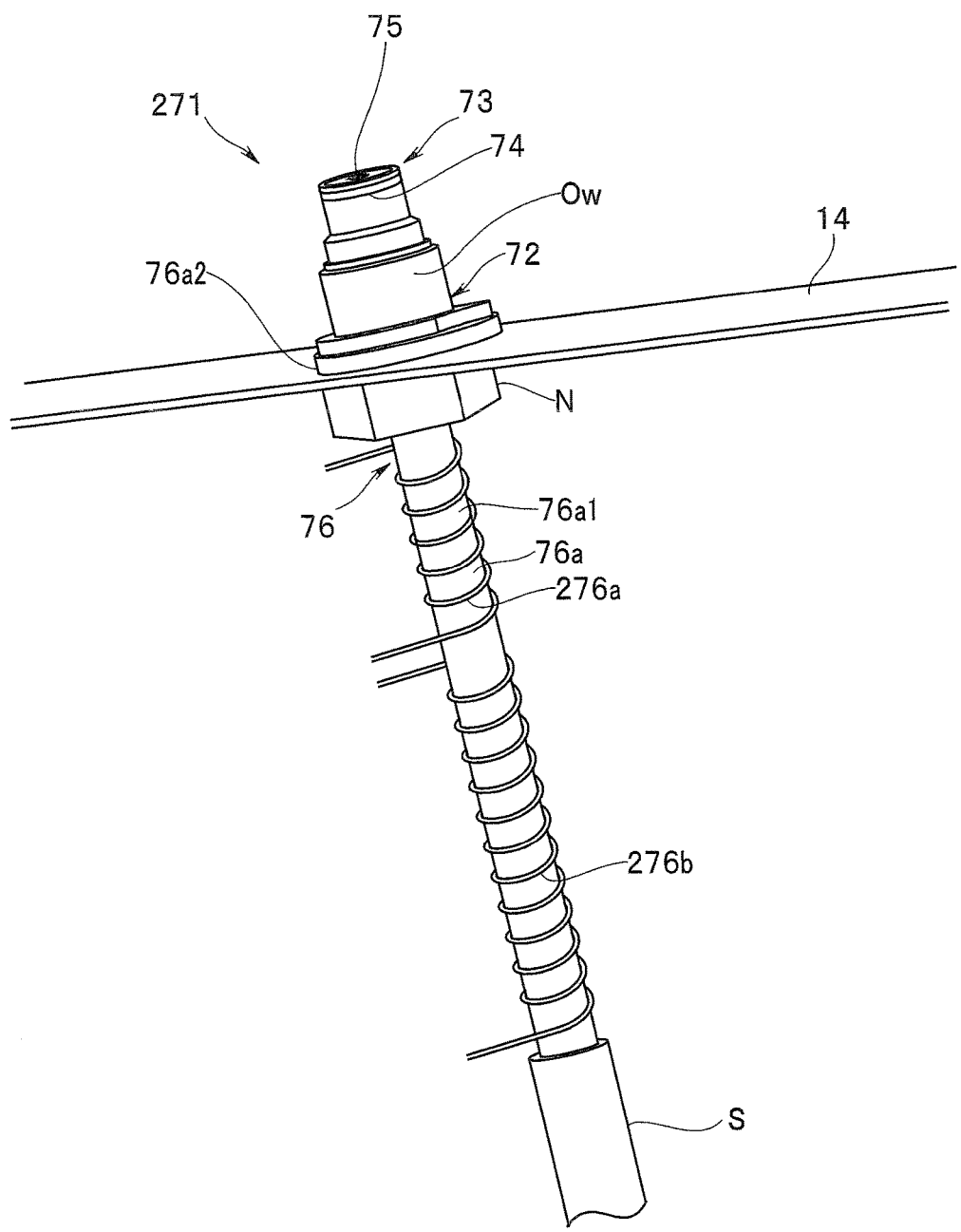
FIG. 8 is a perspective view showing an appearance configuration of a connector of an endoscope reprocessor according to a modified example of the second embodiment of the present invention.

FIG. 8 is a perspective view showing an appearance configuration of a connector 271 of the endoscope reprocessor 2 according to the modified example of the second embodiment of the present invention.

The connector 271 includes coils 276*a* and 276*b*. The number of turns of the coil 276*a* is set to a predetermined number of turns C, and the number of turns of the coil 276*b* is set to a predetermined number of turns D that is larger than the predetermined number of turns C.

The magnetic force switching portion 82 applies current to the coil 276*b* when switching the strength of the electromagnetic attraction force to the first strength, and applies current to the coil 276*a* when switching the strength of the electromagnetic attraction force to the second strength weaker than the first strength. According to such a configuration, the electromagnetic attraction force of the electromagnet 76 can be switched to one of the first strength and the second strength.

According to the above-described modified example of the second embodiment, the strength of the electromagnetic attraction force of the electromagnet 76 is switched by switching the coil to which the current is applied between the coil 276*a* and the coil 276*b*, the number of turns of the coils being different from each other, to thereby enable the outer wall Ow of the connector 271 of the endoscope reprocessor 2 and the inner wall Iw of the connector-side connection portion 121 of the endoscope cleaning tube 111 to be cleaned and disinfected with the fluid at the constant pressure that is sent from the endoscope reprocessor 2 to the endoscope E.

The present invention is not limited to the above-described embodiments and various changes and modifications are possible within a range not departing from the gist of the present invention.

The present invention is capable of providing the endoscope reprocessor, the endoscope cleaning tube, and the endoscope reprocessing unit that are capable of cleaning and disinfecting the connection section with the fluid at the constant pressure that is sent from the endoscope reprocessor to the endoscope.

What is claimed is:

1. An endoscope reprocessing unit comprising:
    a tube, the tube comprising a connector-side connection portion configured to be connected with an endoscope through the tube; and
    an endoscope reprocessor comprising:
        a connector to which the connector-side connection portion is fitted;
        a pump that supplies fluid to the connector, the pump being connected to the connector by a conduit;
        an electromagnet arranged at the connector and including a magnetic material and a coil wound around and fixed to the magnetic material;
        a voltage switching circuit connected to a power source and the coil,
        the voltage switching circuit being configured to switch an output voltage to be outputted to the coil to thereby switch a magnetic force of the electromagnet to at least a first strength and a second strength, the second strength being weaker than the first strength; and
        a processor comprising hardware, the processor being connected to the voltage switching circuit and to the pump, the processor being configured to, while the connector and the connector side connection portion are connected to each other:
            drive the pump so as to supply the fluid to the connector,
            switch the magnetic force of the electromagnet to the second strength so that the connector-side connection portion moves away from the connector by a pressure of the fluid, and
            switch the magnetic force of the electromagnet to the first strength so that the connector-side connection portion is attracted by the magnetic force of the electromagnet to move toward the connector,
        wherein the connector is configured to flow a portion of the fluid to the endoscope via the connector-side connection portion and flow an other portion of the fluid to a gap between an outer wall of the connector and an inner wall of the connector-side connection portion, the gap being formed by the magnetic force being switched to the second strength.

2. The endoscope reprocessing unit according to claim 1, wherein the processor is further configured to alternately switch between the first strength and the second strength by controlling the voltage switching circuit of the electromagnet while driving the pump.

3. The endoscope reprocessing unit according to claim 1, the endoscope reprocessor further comprising:
    a processing tank in which the endoscope is placed;
    a lid portion for opening and closing the processing tank; and
    an open/close detection portion for detecting opening and closing of the lid portion, the open/close detection portion being connected to the processor,
    wherein the connector is arranged on the processing tank,
    the voltage switching circuit is configured to switch the magnetic force of the electromagnet to a third strength weaker than the second strength, and
    the processor is configured to set the strength of the magnetic force of the electromagnet to the third strength by controlling the voltage switching circuit in response to a control signal received from the open/close detection portion, the control signal indicating detection of the opening of the lid portion.

* * * * *